United States Patent [19]

Swyer et al.

[11] Patent Number: 4,457,310
[45] Date of Patent: Jul. 3, 1984

[54] METHOD AND APPARATUS FOR DETERMINING THE ENERGY REQUIREMENTS OF PREMATURE NEWBORNS

[75] Inventors: Paul R. Swyer, Willowdale; Tibor Heim; John M. Smith, both of Toronto, all of Canada

[73] Assignee: The Hospital for Sick Children, Toronto, Canada

[21] Appl. No.: 291,878

[22] Filed: Aug. 11, 1981

[51] Int. Cl.$^3$ .............................................. A61B 5/02
[52] U.S. Cl. .................................. 128/706; 128/668; 128/718; 364/417
[58] Field of Search ............... 128/671, 718, 736, 786, 128/687, 716, 706, 695, 700, 668, 696; 364/417

[56] References Cited
U.S. PATENT DOCUMENTS 4,101,071 7/1978 Brejnik et al. .................. 128/687 X Primary Examiner—Edward M. Coven
Assistant Examiner—John C. Hanley
Attorney, Agent, or Firm—Rogers, Bereskin & Parr

[57] ABSTRACT

A method and apparatus is disclosed for determining the energy requirements of premature newborns. The method includes identifying a series of groups of newborns in which the age and weight of each newborn within each group are within defined ranges. A characteristic mathematical relationship is generated for each group and relates the mean heart rate to the mean energy expenditure over the group. The mean heart rate of a subject newborn, the energy expenditure which is to be determined is measured and applied to the mathematical relationship appropriate to the group into which the subject falls, so as to determine the mean energy expenditure appropriate to that mean heart rate, said expenditure indicating the energy requirement of the subject.

5 Claims, 5 Drawing Figures

METHOD AND APPARATUS FOR DETERMINING THE ENERGY REQUIREMENTS OF PREMATURE NEWBORNS

This invention relates to a method and apparatus for determining the energy requirements of premature human infants (newborns).

In the care and treatment of premature newborns, careful control of calorie intake is necessary in order to ensure proper growth and development, particularly where the infant is significantly premature and/or has medical problems. This control is usually exercised by closely supervising the weight of the infant and, if the infant does not gain weight normally, increasing its daily calorie intake as determined by the professional skill and experience of the supervising medical personnel. At best, control of calorie intake is imprecise even under the most favourable circumstances, not only because questions of judgement are involved, but also because changes in the weight of the infant will normally be very small and may not immediately be detected.

An object of the present invention is to provide an improved method and apparatus for determining the energy requirements of premature newborns.

BRIEF SUMMARY OF THE INVENTION

According to the invention, there is provided a method of determining the energy requirements of premature newborns. The method involves establishing a data base and then comparing against that data base, a subject premature newborn, the energy requirements of which are to be determined. The data base is established by:

(1) identifying a series of groups of newborns in which the age and weight of each newborn within each group are within defined ranges;

(2) measuring the oxygen uptake, the respiratory quotient and the cumulative heart rate of each newborn within each group over a predetermined period;

(3) calculating from said oxygen uptake and said respiratory quotient, the energy expended by each newborn over said predetermined period;

(4) determining the mean energy expended and mean heart rate of each newborn over said predetermined period; and, (5) generating in respect of each group a characteristic mathematical relationship between the mean heart rate and the mean energy expended for each member of said group and calculating the mean of the relationships over the group.

A subject premature newborn is then compared against the data base by:

(1) measuring the cumulative heart rate of the subject over a predetermined period;

(2) determining the mean heart rate of the subject over that period;

(3) determining the said group appropriate to the subject;

(4) applying the mean heart rate of the subject to the mathematical relationship appropriate to that group so as to determine the mean energy expenditure appropriate to that mean heart rate, said expenditure indicating the energy requirement of the subject.

The invention also provides an apparatus for determining the energy requirements of a subject premature newborn from a measurement of the cumulative heart rate of the subject over a predetermined period.

The invention will now be more particularly described with reference to the accompanying drawings, in which:

DETAILED DESCRIPTION

Figure 1:
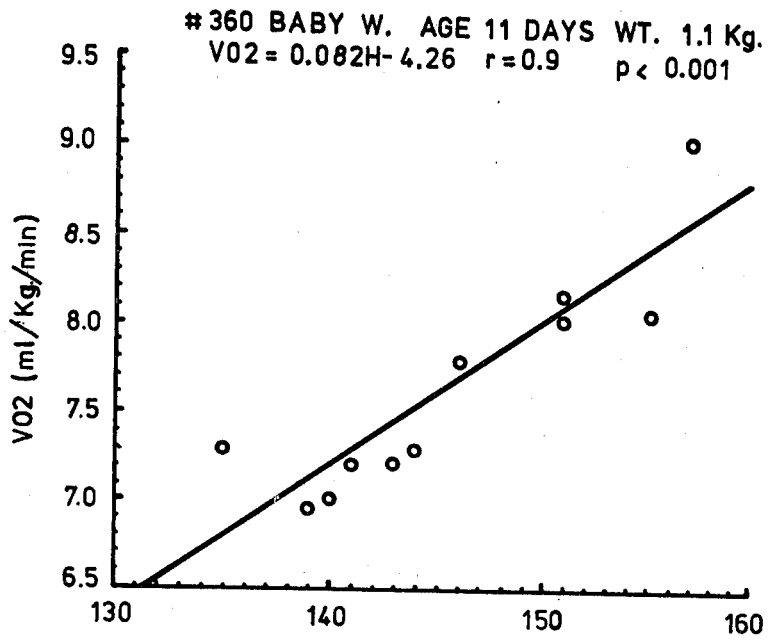
FIG. 1 is a graph showing the relationship between oxygen uptake and mean heart rate over short periods of time for an individual infant.
Figure 2:
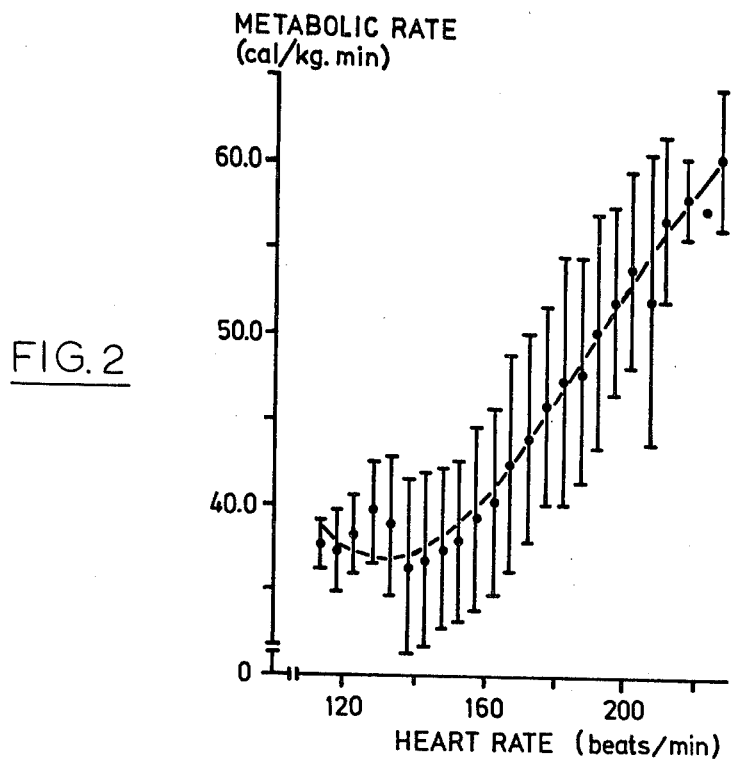
FIG. 2 is a graph showing the relationship between metabolic rate (energy expended) and mean heart rate over short periods of time for members of a first group of newborns.
Figure 3:
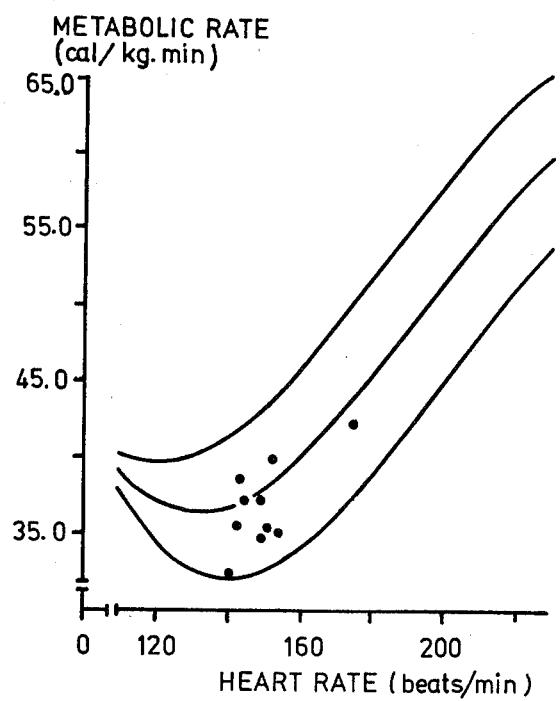
FIG. 3 is a graph similar to FIG. 2 showing the relationship between metabolic rate (energy expended) and mean heart rate for a second group of newborns having age and weight characteristics similar to those of the members of the first group.

FIG. 1 shows an example of an actual graph which was generated during a study of a particular individual newborn. The graph illustrates a definite correlation between heart rate and energy expenditure for that particular individual. FIGS. 2 and 3 are graphs which were generated from studies of groups of infants of which the age and weights were within defined ranges, and show a similar correlation. FIG. 2 represents a typical graph which could actually be used in practice to determine the energy requirements of a particular subject newborn falling into the group in question. Similar graphs would be provided for other groups of newborns having different age and weight characteristics. The manner in which these graphs are generated will be more particularly described later in the sequence in which they were prepared in actual practice. The following description will also indicate how a subject newborn, the energy expenditure of which is to be determined will be compared with the graph appropriate to its age and weight ranges and how the graph will be used to determine its energy requirements.

Actual tests which were conducted in formulating the invention will now be described with particular reference to FIGS. 1, 2 and 3. In all cases, data was acquired by known computerized, open-circuit indirect calorimetry techniques, for example as previously described in Swyer, P. R., Putet, G., Smith, J. M. and Heim, T.: Energy metabolism and substrate utilisation during total parenteral nutrition in the newborn. In: Intensive Care of the Newborn II. Stern, L., Friis-Hansen, B. Eds. Masson Publishing U.S.A. Inc., New York, N.Y., 1978, p 307.

These techniques were used to record oxygen uptake ($VO_2$), carbon dioxide production ($VCO_2$) and respiratory quotient (R) in a thermoneutral incubator environment. Respiratory quotient is defined as a ratio indicating the relation of the volume of carbon dioxide given off in respiration to the volume of oxygen consumed. Cumulative heart beats were measured by on/line ECG monitoring equipment.

Oxygen uptake and cumulative heart rate were initially recorded over short periods of time (15 to 30 minutes) for individual infants displaying variable activities and heart rates. The recorded values were then plotted on a graph of mean heart rate against oxygen uptake and a typical one of such graphs appears as FIG. 1. The plotted co-ordinates for the various periods during which heart rate and oxygen uptake were recorded for that particular individual are shown as circular markings on the graph. A linear regression curve was then generated through the plotted co-ordinates and it will be seen that the graph clearly shows a linear heart rate-energy expenditure correlation within experimental limits (correlation significant to $P<0.001$ level of significance).

FIG. 2 illustrates a characteristic graph which was obtained by plotting mean heart rate against mean metabolic rate (energy expenditure) in respect of a group of newborns, the ages and weights of which were within defined ranges.

Thirty five studies were performed in 16 newborn infants of birthweight (mean $\pm$SD) 1.55$\pm$0.65 kg (range: 0.75 to 3.1 kg) and gestational age 32$\pm$5 weeks (range: 26 to 42 weeks). The mean age at the time of study was 26.5$\pm$15.7 days (range: 5 to 61 days) and the mean weight at the time of study was 1.78$\pm$0.5 kg (range: 0.96 to 2.75 kg). The infants studied fell into 2 groups: 10 orally fed, very low birthweight, premature infants (birthweight 1.18$\pm$0.2 kg; weight at study 1.46$\pm$0.2 kg) and 6 larger babies, receiving total parenteral nutrition following abdominal surgery (birthweight 2.12$\pm$0.7 kg; weight at study 2.11$\pm$0.5 kg). Analysis shows similar results in both groups and they were therefore combined. From these 35 studies relationships between heart rate and metabolic rate (energy expenditure) were defined.

Metabolic rate (energy expenditure) was calculated from the caloric value of $O_2$ for the specific measured respiratory quotient (R). Infants were studied for periods of 1 to 24 hrs (mean 4.5 hrs) and a total of 8269 minute by minute simultaneous measurements of $VO_2$, $VCO_2$, R, metabolic rate and heart rate were recorded during periods of quiet and active sleep as well as awake states and periods of crying. In the case of a newborn having a respiratory quotient of 1, one liter of oxygen represents 5 calories.

The data were evaluated as follows:

(a) Minute by Minute Measurements:

From the minute by minute measurements of heart rate (beats/min) and metabolic rate (cal/kg. min) for all 35 studies combined (8269 measurements), regression analyses were performed to define the relationship between these variables. The data were analysed in 24 defined heart rate categories at intervals of 5 beats per min (111–115, 116–120, ..., 226–230 beats per min) and a regression constructed of the mean metabolic rate (MR) with the corresponding mean heart rate (HR).

(b) Cumulative Heart Rate Measurements:

From the cumulative heart rate and the mean $VO_2$ or mean metabolic rate (MR) recorded over the whole period of the study, the following factors were calculated for each study:

OXYGEN UPTAKE PER HEART BEAT ($\mu$l/kg. beat)=mean $VO_2$ $\times$ duration of study (min)/cumulated heart beats ENERGY EXPENDITURE PER BEAT (cal/kg. beat)=mean MR$\times$ duration of study (min)/cumulated heart beats.

The curve relating mean heart rate and mean metabolic rate $\pm$1 SD is represented in FIG. 2. The line of best fit for all points between 110 to 230 beats/minute is a polynominal distribution to the third degree which is represented by the equation:

$$y = -0.0000291x^3 + 0.01685x^2 - 2.93x + 197.$$

This correlation is highly significant ($r=0.99$; $p<0.001$). From the mean $\pm$SD metabolic rate measured for each heart rate group, a coefficient of variation of 11.5% (range: 4 to 16%) was determined for this curve. Above a heart rate of 140/min (representing 85% of all measurements) there is a highly significant linear relationship between metabolic rate and heart rate:

$$y = 0.29x - 6.1 \ (r=0.0997 \ p<0.001).$$

The flattening of the curve below 140 beats per min suggests that a resting metabolic rate is reached, and can be estimated at 53 kcal/kg. d (222 kJ/kg. d) for this group of infants.

From the cumulative heart rate measurements and mean metabolic rate over the whole study, oxygen uptake per heart beat and metabolic rate per heart beat factors were calculated for individual studies. From these individual results the mean $\pm$SD metabolic rate per heart beat calculated for the whole group:

OXYGEN UPTAKE PER HEART BEAT =51.8$\pm$6.8 $\mu$l $O_2$/kg

ENERGY EXPENDITURE PER BEAT =0.258$\pm$0.03 cal/kg (1.1 J/kg)

The relationship between heart rate and metabolic rate in this specific group of infants is constant with a coefficient of variation of 11.5%.

In order to assess the ability to predict individual energy expenditure by measurement of heart rate, 10 additional studies were performed in a similar population of newborns for periods of 5.5$\pm$1.5 hrs (range: 3 to 7.5 hrs) with continuous monitoring of heart rate during the metabolic study. Using both the polynomial relationship and the constant energy expenditure per heart beat factor determined from the 35 studies, and estimative error of predicting individual metabolic rate was obtained for these 10 additional studies. FIG. 3 shows the previously defined polynomial distribution on which the additional measured metabolic rates and mean heart rates of these 10 studies are plotted. All measurements are within $\pm$1 SD of the original curve and the mean error of estimate is 5.6$\pm$4% (range: $-5$% to $+14$%). Using the factor of 0.258 cal/kg per heart beat, the mean error of estimate was 5.7$\pm$4% (range: $-4$% to $+11.5$%), and the predictive error was less than 10% in 8 of the 10 studies. Further corroboration of the consistency of the HR-MR relationship was derived from a study in a newborn with congenital hyperthyroidism. His mean heart rate of 199 beats/min and measured metabolic rate of 53 cal/kg. min fell on the upper end of the defined curve as shown in FIG. 3 and is represented as a triangle in that view.

The equation identified above or the graphical representation of FIG. 2 may be used in practice to determine the mean energy expenditure appropriate to the mean heart rate of a subject premature newborn whose age and weight are within the ranges of the group.

A similar characteristic graph may be obtained for each of several groups of premature newborns in which the age and weight of each newborn in each group are within defined ranges. In order to determine the energy requirements of a subject premature newborn, the cumulative heart rate of the subject is measured over a predetermined period, and a mean heart rate calculated for that period. A determination is then made as to the group (in terms of age and weight ranges) into which the subject falls. The characteristic graph or equation for that group is then used to determine the metabolic rate (mean energy expenditure) appropriate to the mean heart rate calculated for the subject. This expenditure indicates the energy requirement of the subject (in calories per kilogram of subject weight per minute).

Of course, the vertical (y) axis of the FIG. 2 graph can easily be recalibrated to indicate the daily energy expenditure of the subject infant (as k. cal/kg/day). The daily energy requirements of a particular newborn can then be read directly from this scale.

A characteristic mathematical relationship for a particular group of newborns can of course be mathematically calculated instead of being derived from a graphical representation, for example, wholly or partially using automatic equipment such as computers. For example, a series of graphs of the form shown in FIG. 2 could be generated, one for each group of newborns, by manually plotting results on graph paper or by means of a computer fed with data collected from test groups of newborns. Alternatively, a mathematical calibration factor could be generated either manually or by computer. Having generated this "data base" all that is necessary is to measure the heart rate of a subject newborn and mean the heart rate, determine the group into which the subject falls, and apply the characteristic mathematical relationship for that group to the mean heart rate. Again, this can be done manually by measuring the heart rate, say, using a conventional ECG machine and manually applying the appropriate mathematical relationship. Alternatively, automated equipment could be used. For example, an ECG machine could be modified to automatically mean the heart rate of a subject and apply the appropriate mathematical relationship to give a direct readout of energy requirements. The machine would be provided with an appropriate selector (such as a rotary dial) for indicating the particular group into which the subject falls. The supervisory medical personnel would adjust the selector to indicate the particular group and the machine would then automatically apply the appropriate mathematical relationship to the mean heart rate of the subject to provide a direct indication of the daily calorific requirements of the subject.

Figure 4:
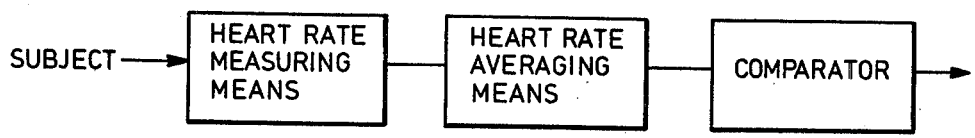
FIGS. 4 and 5 are block diagrams illustrating two alternative forms of apparatus for determining the energy requirements of premature newborns according to the invention.
Figure 5:
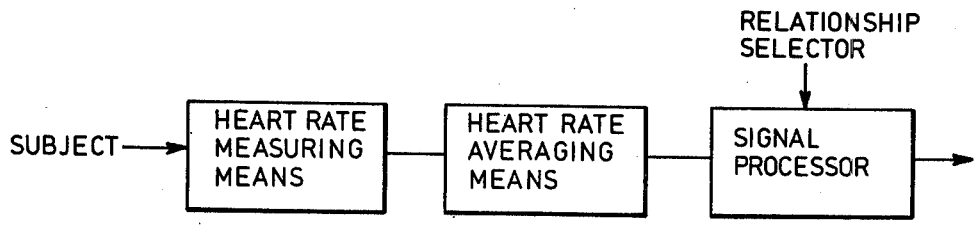

By way of example, FIGS. 4 and 5 are block diagrams illustrating alternative forms of apparatus which may be provided for determining the energy requirements of premature newborns in accordance with the invention. Suitable electronic equipment for performing the various functions indicated by the block diagrams will be readily apparent to a person skilled in the art.

The apparatus shown in FIG. 4 includes a heart rate measuring unit which may be represented by a conventional ECG machine. A heart rate averaging unit receives measurement of the cumulative heart rate of a subject premature newborn over a predetermined period and determines the mean heart rate of the subject over that period. The apparatus further comprises comparator means which compares this mean heart rate to a predetermined linear relationship established for the appropriate group of newborns, equivalent to a graphic representation as in FIG. 3. The comparator means will include a selector by which the appropriate linear relationship can be selected from a series of such relationships for various groups of newborns. The energy requirement of the subject premature newborn is then directly indicated by the comparator means, e.g. by a digital display.

FIG. 5 illustrates an alternate form of the apparatus in which the comparator means of FIG. 4 is replaced by signal processing means for determining the the mean energy expenditure appropriate to the mean heart rate received from the heart rate averaging unit. The signal processing means calculates the energy requirement in accordance with the mathematical relationship established for the appropriate group of newborns and directly indicates the energy requirement of the subject. Again, appropriate selector means will be provided so that the appropriate mathematical relationship can be chosen from a series of such relationships.

Alternative means of implementation would use an electronic computing device to calculate metabolic rate from the value of mean heart rate using the equations relating these variables. This would permit the calculation of metabolic rates over short time intervals (e.g. 1 minute) which would in turn be summed to provide a more accurate estimate of energy expenditure over long time periods (e.g. several hours).

Apparatus of the form generally shown in FIGS. 4 and 5 can of course be directly incorporated into a conventional ECG machine or can be designed as a separate unit to receive a heart rate input from an ECG machine.

It will of course be understood that the particular units referred to above are not to be considered as limitive. Appropriate scale factors can of course be applied, e.g. to express cal/kg/min as cal/kg/day.

We claim:

1. Apparatus for determining the energy requirements of a subject premature newborn from a measurement of the cummulative heat rate of the subject over a predetermined period, wherein the birthweight of the subject is within the range 0.75 to 3.1 kg. and the gestational age of the subject is within the range 26 to 42 weeks, the apparatus comprising:
   heart rate averaging means adapted to receive said measurement and to determine the mean heart rate of the subject over said predetermined period; and,
   means adapted to apply said mean heart rate to a characteristic mathematical relationship defined by the following equation and to provide a resulting output signal representing the mean energy expenditure appropriate to the applied mean heart rate of the subject:

$$y = -0.0000291x^3 + 0.01685x^2 - 2.93x + 197$$

in which:
   x represents the mean heart rate of the subject in beats per minute and,
   y represents the energy expenditure of the subject in calories per kilogram per minute.

2. Apparatus as claimed in claim 1, further comprising heart rate measuring means in the form of an electro-cardiogram machine adapted to directly measure the cumulative heart rate of a subject and to provide said measurement directly to said heart rate averaging means.

3. Apparatus as claimed in claim 1, wherein said means adapted to apply said mean heart rate applies the following equation:

y=0.29X−6.1 for X>140.

4. A method of determining the energy requirements of premature newborns each having a birthweight in the range 0.75 to 3.1 kg and a gestational age in the range 26 to 42 weeks comprising the steps of:
(1) measuring the cumulative heart rate of a subject premature newborn over a predetermined period;
(2) determining the mean heart rate of the subject over that period;
(3) applying the mean heart rate of the subject to the following mathematical relationship and determining from said relationship the mean energy expenditure appropriate to that mean heart rate:

y=−0.0000291x³+0.01685x²−2.93x+197 in which:
x represents the mean heart rate of the subject in beats per minute and,
y represents the energy expenditure of the subject in calories per kilogram per minute.

5. A method as claimed in claim 4, where in the step of applying the mean energy expenditure is determined from the following mathematical relationship:
y=0.29X−6.1 for X>140.